(12) United States Patent
Fitton

(10) Patent No.: US 6,966,319 B2
(45) Date of Patent: *Nov. 22, 2005

(54) ANATOMICAL MOUTHPIECE WITH RETAINING WINGS SYSTEM AND METHOD

(76) Inventor: Russell P. Fitton, 820 S. Northwest Hwy., Barrington, IL (US) 60010

( * ) Notice: Subject to any disclaimer, the term of this patent is extended or adjusted under 35 U.S.C. 154(b) by 0 days.

This patent is subject to a terminal disclaimer.

(21) Appl. No.: 10/376,658

(22) Filed: Feb. 28, 2003

(65) Prior Publication Data

US 2003/0150450 A1 Aug. 14, 2003

Related U.S. Application Data

(63) Continuation-in-part of application No. 09/881,338, filed on Jun. 14, 2001, now Pat. No. 6,536,424.

(51) Int. Cl.[7] .............................................. A61F 13/00
(52) U.S. Cl. ....................... 128/848; 128/859; 602/902
(58) Field of Search ..................... 128/200.24, 200.26, 128/200.29, 201.11, 201.26, 201.27, 201.28, 128/205.24, 206.29, 207.12, 207.14, 207.18, 128/849, 859–862, 848; 433/6, 140; 602/902; 600/237–240

(56) References Cited

U.S. PATENT DOCUMENTS

| | | | | |
|---|---|---|---|---|
| 2,142,614 | A | * | 1/1939 | Mitchell ...................... 27/21.1 |
| 3,303,845 | A | * | 2/1967 | Detmer, III ............ 128/202.28 |
| 3,603,306 | A | | 9/1971 | Bonin, Jr. |
| 3,692,025 | A | * | 9/1972 | Greenberg .................. 128/857 |
| 3,818,906 | A | * | 6/1974 | Stubbs ........................ 606/234 |
| 3,844,281 | A | | 10/1974 | Shamlian |
| 4,230,106 | A | | 10/1980 | Geeslin et al. |
| 4,862,903 | A | | 9/1989 | Campbell |
| 5,052,410 | A | * | 10/1991 | Stubbs ........................ 128/859 |
| 5,062,422 | A | | 11/1991 | Kinkade |
| 5,069,206 | A | * | 12/1991 | Crosbie .................. 128/207.17 |
| 5,117,817 | A | | 6/1992 | Lin |
| 5,203,324 | A | | 4/1993 | Kinkade |
| 5,305,741 | A | | 4/1994 | Moles |
| 5,438,978 | A | | 8/1995 | Hardester, III |
| 5,590,643 | A | * | 1/1997 | Flam ...................... 128/200.26 |
| 5,642,738 | A | * | 7/1997 | Lilly, Jr. ...................... 128/848 |
| 5,701,885 | A | | 12/1997 | Hale |
| 5,720,302 | A | * | 2/1998 | Belfer ......................... 128/848 |
| 5,865,170 | A | | 2/1999 | Moles |
| 6,269,816 | B1 | * | 8/2001 | Rigonatti et al. ........... 128/859 |
| D452,011 | S | * | 12/2001 | Redhage .................... D24/181 |
| 6,371,108 | B1 | | 4/2002 | Christianson |
| 6,514,176 | B1 | * | 2/2003 | Norton ......................... 482/11 |
| 6,517,549 | B1 | * | 2/2003 | Dennis ....................... 606/108 |
| 6,536,424 | B2 | * | 3/2003 | Fitton .................... 128/200.24 |

(Continued)

FOREIGN PATENT DOCUMENTS

DE 1 220 738 7/1966

(Continued)

OTHER PUBLICATIONS

Barclay, Laurie, "Scuba Mouthpiece Can Cause Jaw and Dental Problems" *Web*MDHealth, available at http://my-.webmd.com/content/article/1676.52711, pp. 1-3; visited May 14, 2001.

*Primary Examiner*—Teena Mitchell
(74) *Attorney, Agent, or Firm*—Brinks Hofer Gilson & Lione

(57) ABSTRACT

A mouthpiece includes a wall having an anterior section and a plurality of posterior sections. Retaining wings are coupled to the anterior section. The retaining wings conform to the anatomy of the user's buccal vestibule. The method of customizing the mouthpiece includes cutting the retaining wings.

11 Claims, 7 Drawing Sheets

U.S. PATENT DOCUMENTS

| | | | |
|---|---|---|---|
| 6,571,798 B1 * | 6/2003 | Thornton | 128/206.21 |
| D479,876 S * | 9/2003 | Gradon et al. | D24/110.5 |
| 6,679,257 B1 * | 1/2004 | Robertson et al. | 128/204.18 |
| 2003/0089371 A1 | 5/2003 | Robertson et al. | |

FOREIGN PATENT DOCUMENTS

| | | |
|---|---|---|
| WO | WO 96/03173 | 8/1996 |
| WO | WO 00/45895 | 8/2000 |

* cited by examiner

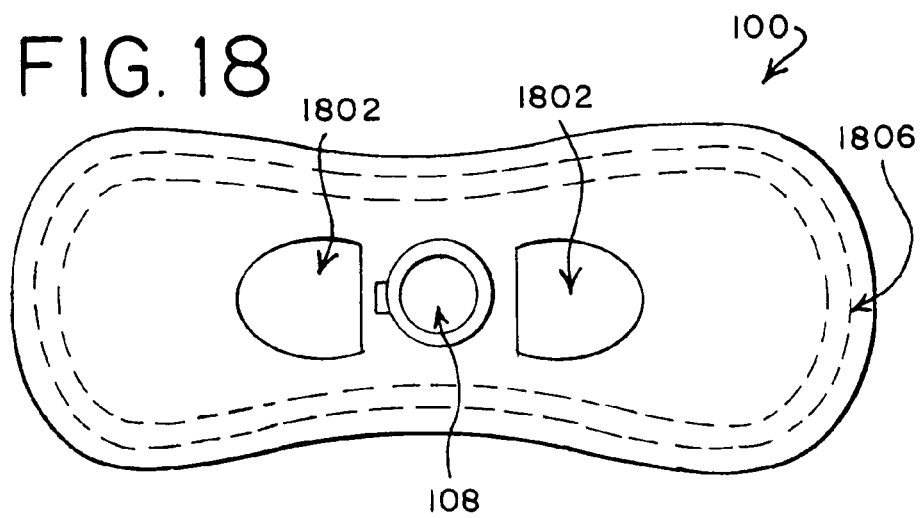
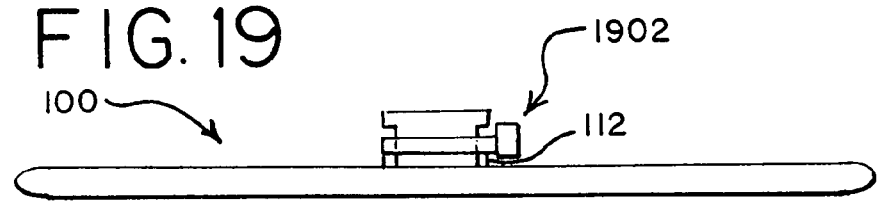
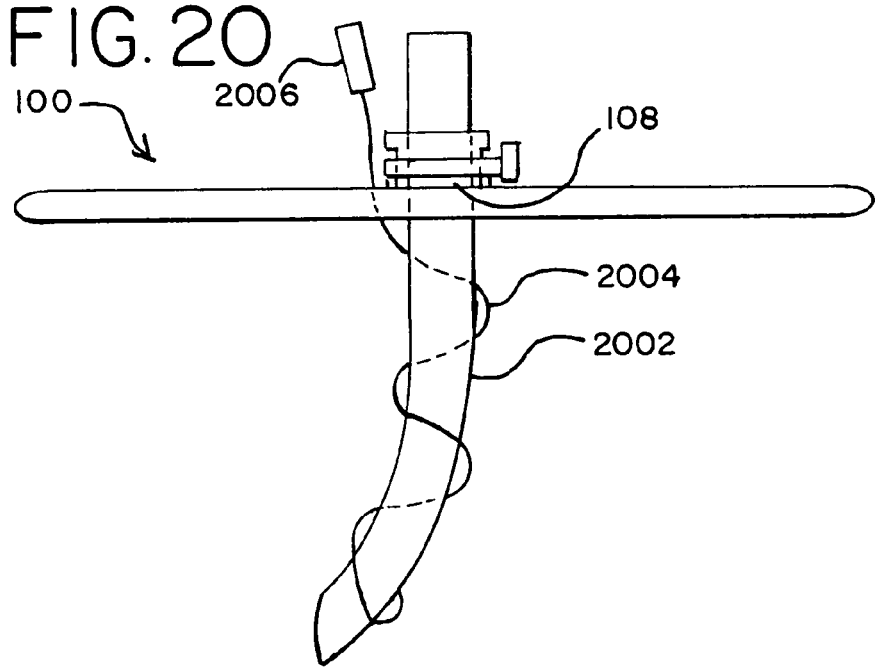

US 6,966,319 B2

ANATOMICAL MOUTHPIECE WITH RETAINING WINGS SYSTEM AND METHOD

RELATED APPLICATION

This application is a continuation-in-part of application Ser. No. 09/881,338, entitled "Anatomical Mouthpiece with Retaining Wings and Method of Use" filed Jun. 14, 2001 now U.S. Pat. No. 6,536,424, and which is hereby incorporated by reference in its entirety.

BACKGROUND

This invention relates to a mouthpiece, and more particularly, to a mouthpiece and method of use for breathing or medical treatments.

Mouthpieces allow users to breath from an apparatus that delivers gas. In some medical devices, mouthpieces allow for the infusion of gas to oxygenate the lungs and expiratory pressures that draw carbon dioxide and other gases from the lungs. In underwater uses, mouthpieces allow swimmers to breath from an apparatus that delivers gas at the same pressure as the surrounding water.

Some underwater mouthpieces have not changed over a long period of time. Bite blocks gripped by front and middle teeth can be used to secure some mouthpieces to the interior cavity of the mouth. This gripping pressure by the front and middle teeth can cause joint stress and inflammation. A prolonged use can result in temporomandibular joint syndrome that generates symptoms such as severe headaches, muscle fatigue, facial pain, and ringing in the ears. When underwater mouthpieces affect swimmers' ears, balance can be affected and underwater accidents such as drowning can occur. In addition, underwater mouthpieces can result in gum abrasions, bone loss, and damage to restorative dental work.

Some underwater mouthpieces can also add significant resistance to swimmers' respiratory systems. Because these underwater mouthpieces are retained by clenched jaws the normal movement of airflow through the mouth is reduced. This decreased ventilation is complicated by the diminished breathing capacity that occurs with changes in water depth. Accordingly, carbon dioxide levels in swimmers can increase which impair swimmers' consciousness and can lead to drowning. The present invention is directed to a mouthpiece, a method of use, and a method of customizing a mouthpiece to a user's mouth that overcomes some of these potential drawbacks in the prior art.

BRIEF DESCRIPTION OF THE DRAWINGS

In the figures, like reference numerals designate similar parts throughout several views.

FIG. 18 is a front side view of a presently preferred alternative embodiment with openings to provide access for oral and intubation tubes.

FIG. 19 is a side view of a presently preferred alternative embodiment with a holding device.

FIG. 20 is a side view of a presently preferred alternative embodiment coupled to an intubation tube.

SUMMARY

A presently preferred mouthpiece includes a wall having an anterior and a posterior section. The anterior and posterior sections have an inner surface that is adapted to be positioned adjacent to a dental arch. Retaining wings are coupled to the anterior section. The retaining wings include a portion that encloses a portion of an orifice and a portion that conforms to the anatomy of a user's buccal vestibule. A presently preferred method of customizing a mouthpiece includes grasping the mouthpiece and cutting the retaining wings to fit within a user's mouth.

DETAILED DESCRIPTION OF THE PRESENTLY PREFERRED EMBODIMENTS

The presently preferred mouthpiece is a device that facilitates breathing. In medical treatments, the presently preferred mouthpiece allows devices and peripheral systems to deliver oxygen and other treatments to the lungs and remove carbon dioxide or other by-products from the lungs. The presently preferred mouthpiece facilitates fluid flow to the lungs. In underwater uses, the presently preferred mouthpiece allows swimmers to breath underwater for extended periods of time. The mouthpiece reduces the breathing resistance of some prior art mouthpieces.

Figure 1:
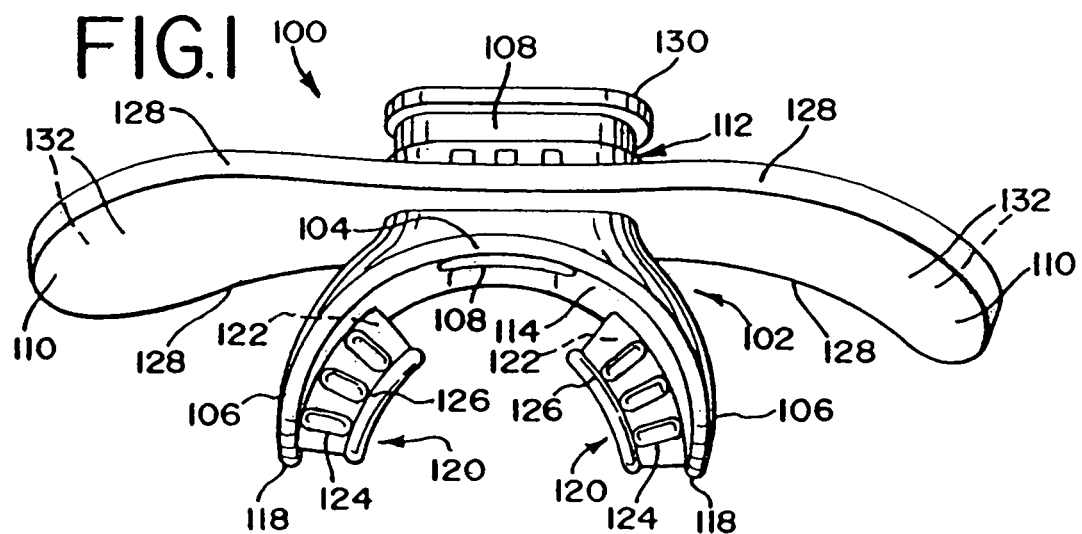
FIG. 1 is a side perspective view of a presently preferred embodiment.

FIG. 1 is a perspective view of a presently preferred embodiment. The presently preferred mouthpiece 100 comprises a continuous peripheral flexible wall 102 having an anterior section 104 and a plurality of posterior sections 106. Preferably, the inner and outer surfaces of the anterior and posterior sections 104 and 106 are customized to the anatomy of a user's upper and lower dental arches. Preferably, the posterior sections 106 have substantially smaller heights than the anterior section 104. As shown, the height of the anterior section 104 tapers down to the shorter heights of the posterior sections 106. Preferably, the anterior section 104 encloses an orifice 108 that passes through the anterior section 104 and retaining wings 110. Preferably, the orifice 108 is partially enclosed by a neck 112 that projects from an outer surface of the anterior section 104.

Preferably, the inner surfaces of the anterior and posterior sections 104 and 106 have a U-shape. A curved channel 114 extends along the inner surfaces from the orifice 108 to the ends 118 of the posterior sections 106. Preferably, the curved channel 114 aligns with a user's exterior dental curve from a central incisor to a third molar. As shown, a plurality of bitewings 120 divide a portion of the curved channel 114 into upper and lower channels at intermediate positions between the anterior section 104 and the ends 118 of the posterior sections 106. Each bitewing 120 includes a pair of upper and lower surfaces 122 and 124 that extend inward to an adjoining wall 126. While the upper and lower surfaces 122 and 124 of the bitewings 120 are shown substantially flat in FIG. 1, alternative presently preferred embodiments can include contoured upper and/or lower surfaces 122 and 124. For example, referring to FIGS. 2, 3, 7, and 11, the contour can comprise spaced apart upper and lower recesses. Preferably, the recesses have a substantially curved or elliptical shape angled to the user's upper and lower dental arch. More preferably, the recesses are fitted to a user's upper and lower molars and bicuspids. In another presently preferred alternative embodiment, the recesses can be positioned exclusively on the upper or lower surfaces 122 and 124, or on any combination of the upper and lower surfaces 122 and 124 of the bitewings 120.

Referring to FIG. 1, preferably the upper and lower surfaces 122 and 124 of the bitewings 120 include a curved transition to a portion of the inner surfaces of the posterior sections 106 and the adjoining wall 126. Preferably, the height of the adjoining wall 126 varies with the user's anatomy. Preferably, the adjoining wall 126 is spaced apart from the inner surface of the posterior section 106 and can be aligned with the inner dental curve or inner dental arch of the user. In the presently preferred embodiment, preferably the adjoining wall 126 can be positioned adjacent to or in contact with the inner surfaces of the user's molars or bicuspids.

Figure 4:
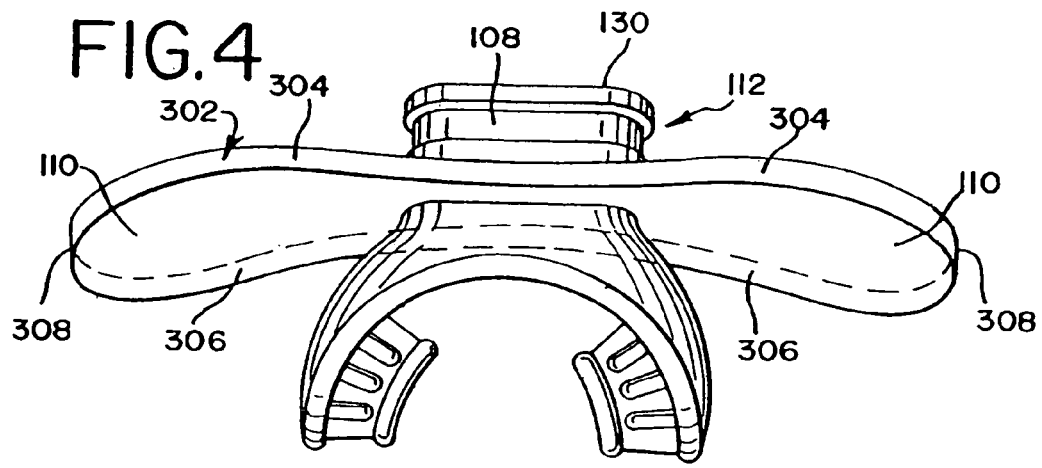
FIG. 4 is a second side perspective view of the presently preferred embodiment.
Figure 9:
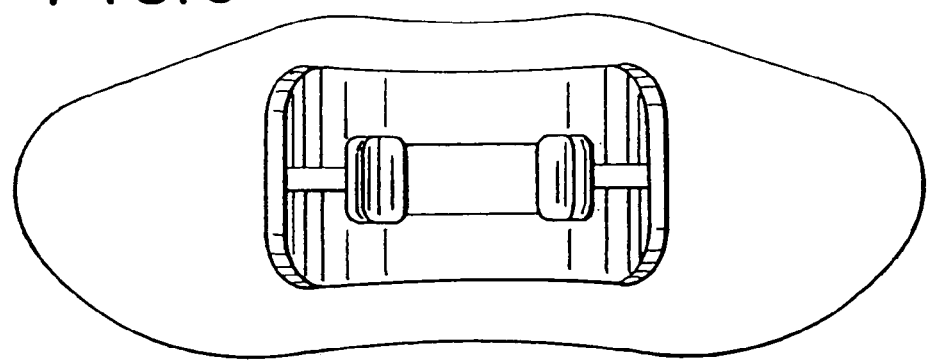
FIG. 9 is a rear view of FIG. 1.

Preferably, the retaining wings 110 have a substantially obround shape framed by a continuous surface 128 that can be positioned within a labial and buccal vestibule of the user. The labial and buccal vestibule is bounded in front and laterally by the user's lips and the continuous mucous membrane that lines the interior of the user's cheeks and behind and internally by the gums and teeth of the user's upper and lower jaws. As shown in FIGS. 4 and 9, preferably the upper rim 304 and the lower rim 306 of the retaining wings 110 each include double curve surfaces. The double curve surfaces comprise a concave surface joined to a pair of convex surfaces. In cross-section, the double curve surfaces are formed by the unison of a pair of convex lines to a concave line. Although portions of each double curve surface are symmetrical about a plane 1002 shown in cross-section in FIGS. 10 and 12 passing through or near a center of the retaining wings 110, in presently preferred alternative embodiments other shapes, symmetries, or lack of symmetry can be used. As shown in FIG. 4, preferably the upper, lower, and side rims 304, 306, and 308 that comprise a circular rim 302 allow the retaining wings 110 to substantially conform to the user's transition between the mucous membrane and the gums.

Referring to FIGS. 1–5 and 7, the retaining wings 110 are coupled to the neck 112 at a position intermediate of the anterior section 104 and a proximal rim 130. Alternatively, the retaining wings 110 can be a unitary part of or coupled to the anterior section 104. The retaining wings 110 comprise a pair of substantially flat surfaces 132 that are interconnected at the circular rim 302. Preferably, the retaining wings 110 are comprised of a substantially elastic material. In the presently preferred embodiments, the retaining wings 110 bias the user's lips and the continuous mucous membrane that lines the inner surfaces of the user's cheeks away from the gums and teeth of the user's upper and lower jaws. Preferably, the bias of the retaining wings 110 increases as a continuous flow of fluids, such as compressed air passes through the orifice 108 into the user's mouth. In this presently preferred embodiment, the retaining wings 110 functions like a valve that allows the flow of fluids only through the orifice 108 when the user's labial and buccal vestibule is pressurized. It is this bias that spreads out the cheeks of the user and facilitates the user's orapharynx to relax and open, which facilitates unrestricted fluid flow.

Preferably, the outer periphery of the neck 112 is surrounded by a plurality of rings. Preferably, one of the rings extends away from the orifice and forms the proximal rim 130 that is positioned near the proximal end of the neck 112. Preferably, the rings allow the presently preferred embodiments to couple other devices including, for example, a fluid line such as a compressed gas line.

Figure 2:
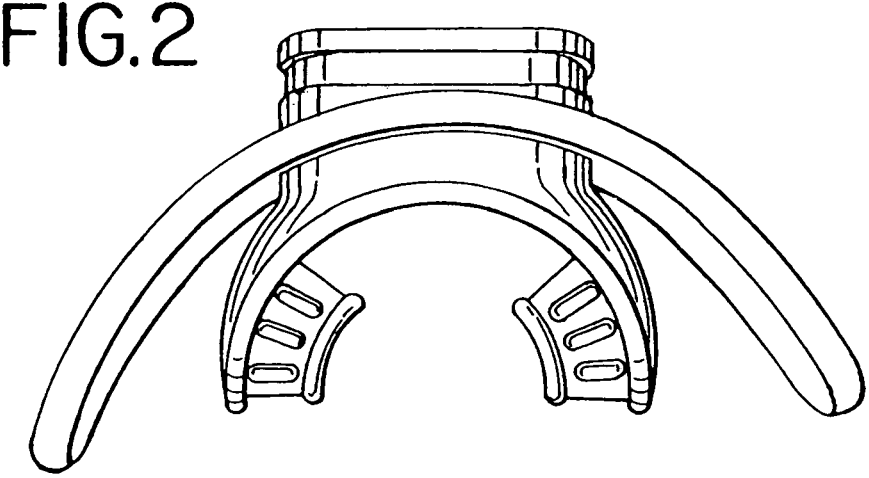
FIG. 2 is a top view of FIG. 1.
Figure 3:
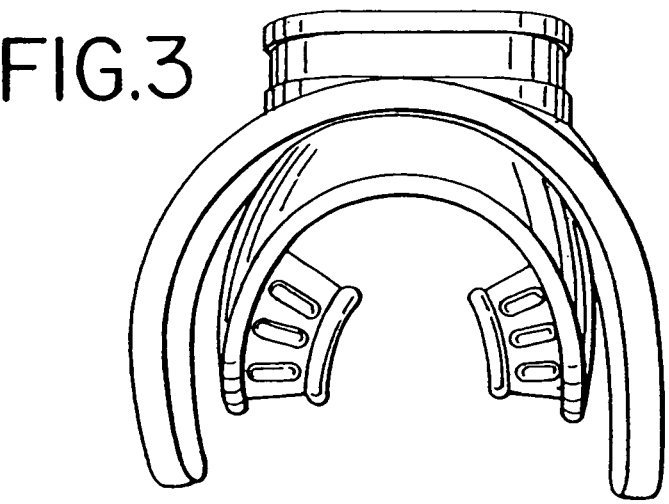
FIG. 3 is a second a top view of FIG. 1.
Figure 6:
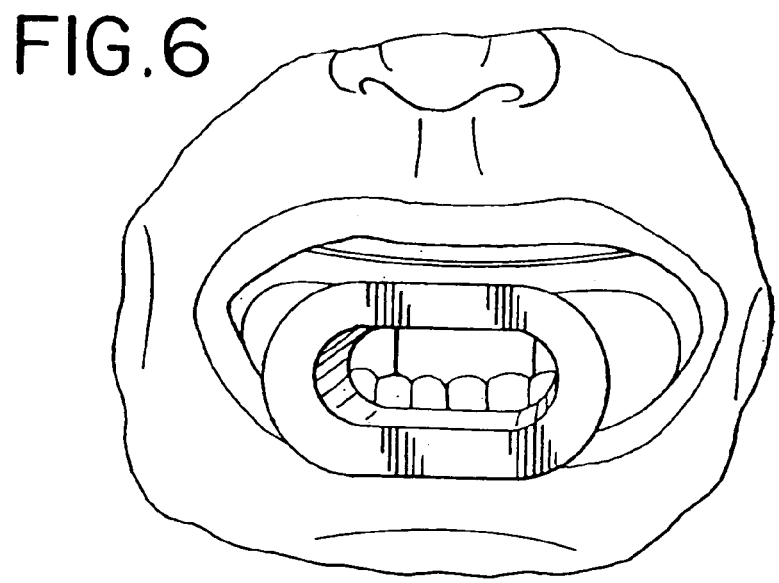
FIG. 6 is a side view of FIG. 1 retained in a user's mouth.
Figure 7:
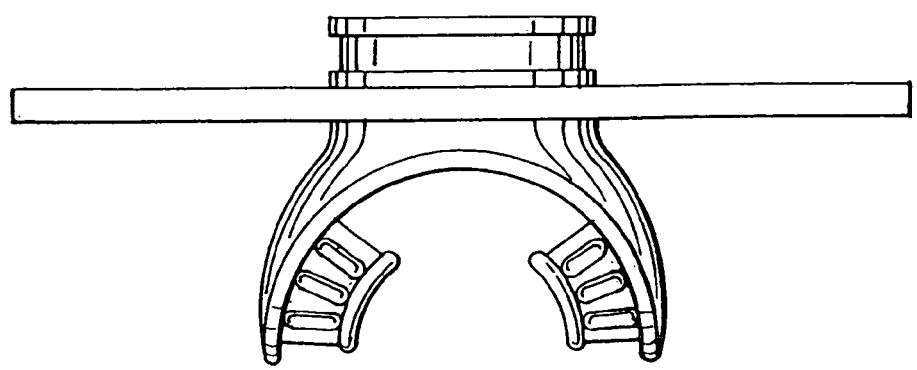
FIG. 7 is a third side perspective view of the presently preferred embodiment of FIG. 1.
Figure 8:
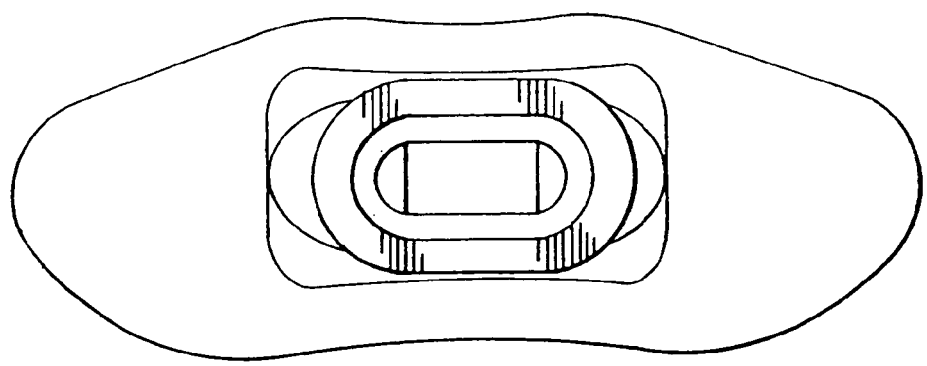
FIG. 8 is a front side view of FIG. 1.

The function of the presently preferred embodiments is illustrated in FIGS. 2, 3, and 6. FIGS. 2 and 3 illustrate the bending of the retaining wings 110 toward the ends 118 of the posterior sections 106. While the retaining wings 110 can be flexed and extended to any length to facilitate a seal or insertion into a user's mouth, as shown the retaining wings 110 extend beyond the ends 118 of the posterior sections 106. Referring to FIGS. 4 and 6, an upper and a lower rim 304 and 306 of the retaining wings 110 are tucked in back of the user's upper and lower lips. Preferably, the side rims 308 of the retaining wings 110 can extend back and adjacent to second or third molars of the user's upper and lower jaws. Preferably when seated in the user's mouth, the bitewings 120 are substantially fitted to the user's occlusal surfaces of one or more bicuspids and/or molars.

Figure 10:
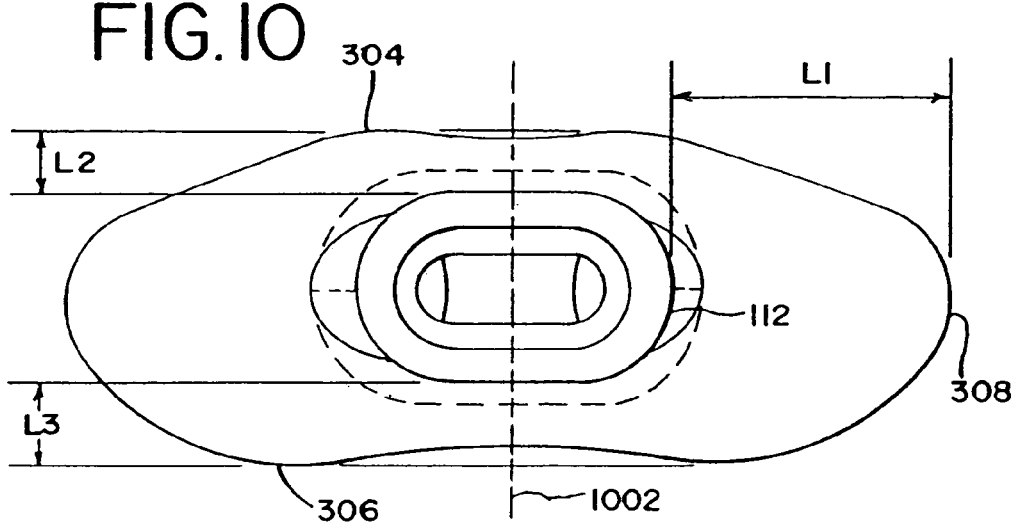
FIG. 10 is a second front view of FIG. 1.
Figure 11:
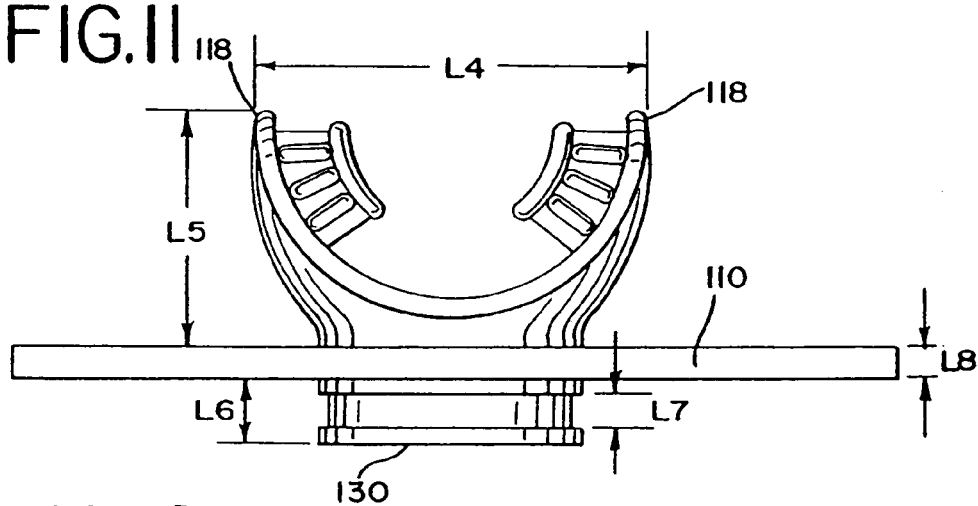
FIG. 11 is a third top view of FIG. 1.
Figure 12:
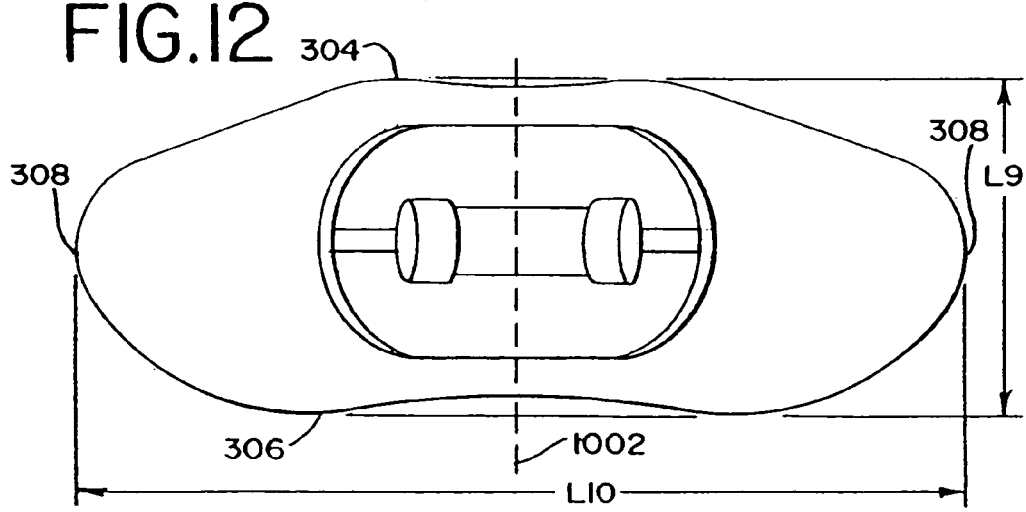
FIG. 12 is a second rear view of FIG. 1.

Although the claims are not limited to specific dimensions, FIGS. 10–12 illustrate the dimensions of a presently preferred exemplary embodiment. Preferably, L1 is the distance between a side surface of the neck 112 and the side rim 308. Preferably, L2 is the longest distance between an upper surface of the neck 112 and the upper rim 304 and L3 is the longest distance between a lower surface of the neck 112 and the lower rim 306. Preferably, L4 is the distance that separates the ends 118 of the posterior sections 106. Preferably, L5 is the distance between the ends 118 of the posterior sections 106 and a first side surface of the retaining wing 110. Preferably, L6 is the distance between an end of the proximal rim and a second side surface of the retaining wing 110. Preferably, L7 is the distance of a recess positioned between the proximal rim 130 and a second rim. Preferably, L8 is the width of the retaining wing 110. Preferably, L9 is the longest distance between the upper and lower rims 304 and 306. Preferably, L10 is the distance between side rims 308. In the exemplary embodiment illustrated in FIGS. 10–12, L1 is about 48 mm, L2 and L3 are about 14 mm, L4 is about 48 mm, L5 is about 33 mm, L6 is about 10 mm, L7 is about 4 mm, L8 is about 1.5 mm, L9 is about 46 mm, and L10 is about 130 mm. Many other dimensions are possible as the mouthpiece 100 can be made to many other dimensions.

Figure 5:
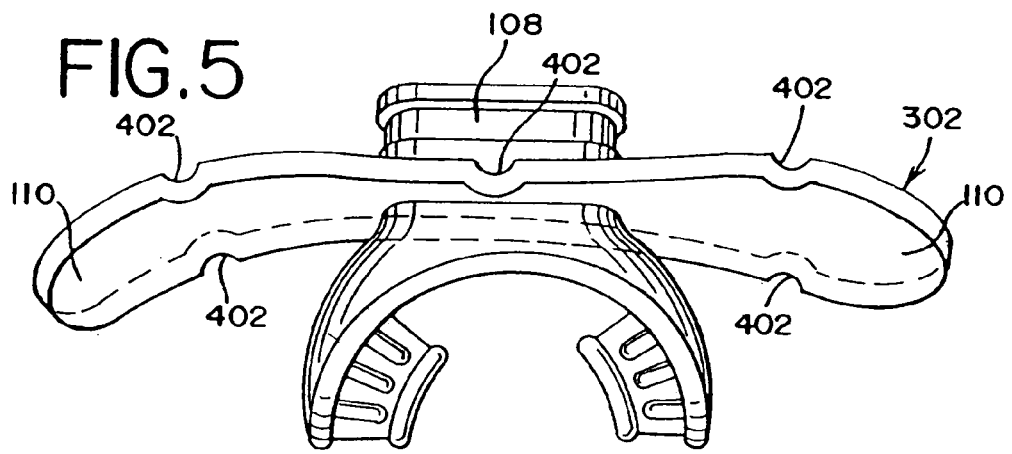
FIG. 5 is a side perspective view of a presently preferred alternative embodiment.

The above-described presently preferred embodiments can be modified into many alternative preferred embodiments. For instance, the retaining wings 110 can be a one piece structure or formed of multiple parts and each of the presently preferred retaining wings 110 can assume many other shapes. Preferably, the shape of the retaining wings 110 conforms to the surfaces that bound the labial and buccal vestibule that extends between the user's upper and lower jaws and the interior surfaces of the user's cheeks and lips. Furthermore, as shown in FIG. 5 the circular rim 302 that frames the retaining wings 110 can comprise substantially U-shaped notches 402 at the front and intermediate sections of the retaining wings 110. Preferably, the substantially U-shaped notches 402 can be positioned near the frenum, which are folds of mucous membrane positioned in the front and sides of the user's upper and lower jaws. In yet another presently preferred alternative embodiment, the above-described mouthpiece does not include bitewings 120. In this case, the alternative presently preferred embodiment is retained by the bias of the retaining wings 110 and the anterior and posterior sections 104 and 106. Alternatively, when bitewings 120 are used, the upper and lower surfaces 122 and 124 of the bitewings 120 can comprise a self-setting acrylic that conforms to the occlusal surfaces and/or portions of the user's teeth. Similarly, the presently preferred mouthpiece 100 can be customized to a user's mouth or made to selected dimensions.

Moreover, the invention is not limited to the particular retaining wings 110 described above. Any suitable retaining wing can be used. For instance, the circular rim 302 that preferably frames the retaining wings 110 can comprise multiple rims positioned adjacent or spaced apart from one another. Preferably, at least one of the rims forms a seal with the mucous membrane that lines the interior of the user's cheeks and the user's gums. Because a preferred function of one of the rims can be to provide means that facilitates insertion and removal of the presently preferred mouthpiece 100 from a user's mouth, each of the rims can have many other shapes including but limited to elliptical, cylindrical, arcuate, and other shapes. In some alternative presently preferred embodiments, at least one of the multiple rims can include U-shaped notches at the front and intermediate sections of the retaining wings 110.

The above-described presently preferred embodiments can be used within many devices including medical, fire fighting, emergency services, and underwater breathing systems. The above-described mouthpieces can communicate with, form a unitary part of, or be integrated within a standard, modular, or self-contained anesthetic system, firefighter breathing system, ventilator, inhaler, snorkel, regulator, scuba system, underwater system, emergency system, medical breathing system and/or any other therapeutic or corrective treatment system. The above-described mouthpieces can also be used to treat sleeping disorders. Sleeping is a complex behavior that is part of the body's adaptation to changes, such as changes in light and temperature. Sleep is not always benign as it can be susceptible to disorders and disease. Just as a sleep patterns can vary over a person's life, the diversity of sleep disorders can also vary. A difficulty falling a sleep, a difficulty staying awake, and abnormal movements that can occur in the depth of sleep can all be problematic. Sleep apnea is one sleeping disorder that can have characteristic of all three of these problems. Sleep apnea sufferers can have a tendency to stop breathing when they are a sleep. As their oxygen hunger increases, these sufferers can make gasping efforts to receive air causing their airways to close and pushing them closer to self-strangulation.

Figure 13:
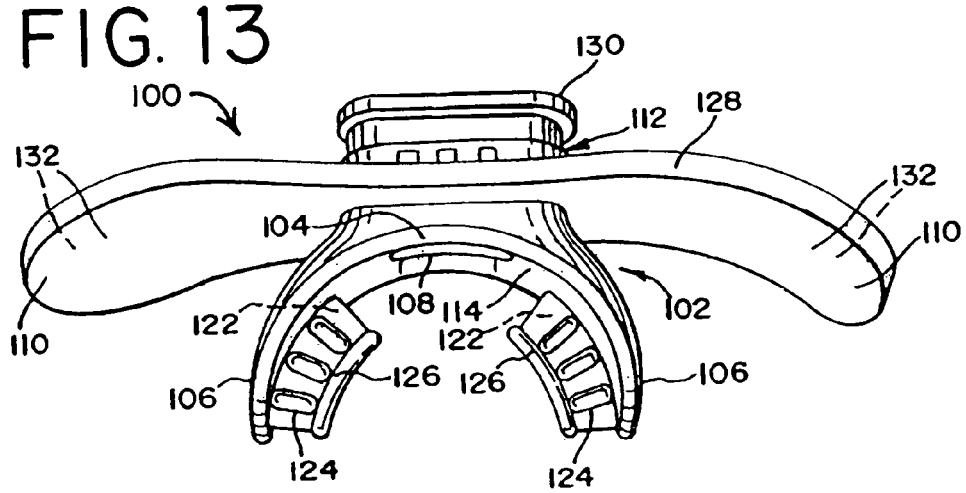
FIG. 13 is a side perspective view of a presently preferred alternative embodiment.
Figure 14:
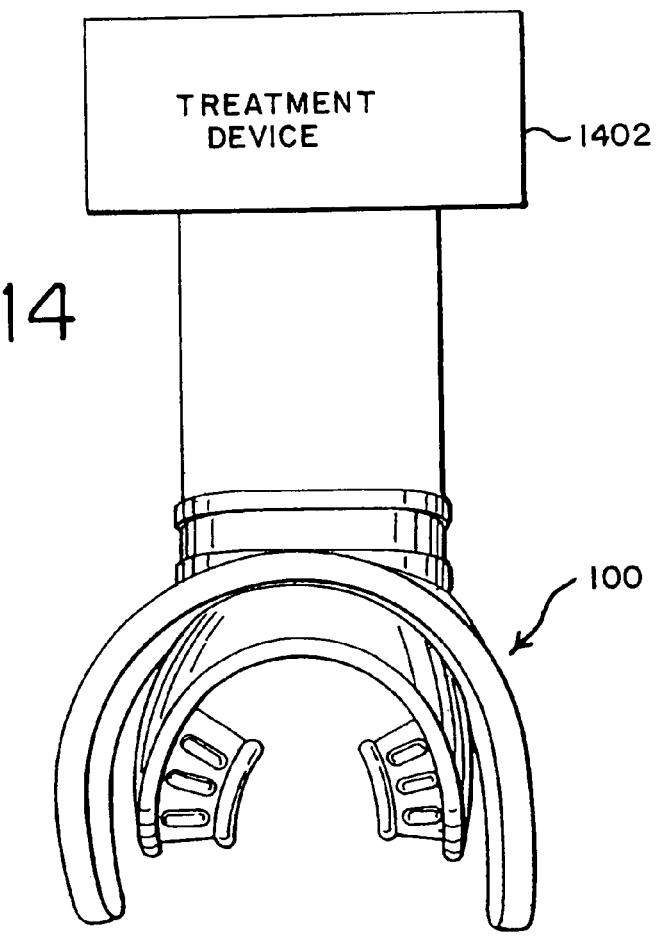
FIG. 14 is a side perspective view of FIG. 13 coupled to a treatment device.

An effective treatment of sleep apnea and other sleeping disorders such as snoring, for example, can include a positive airway pressure therapy that uses a treatment device coupled to an oral appliance or an oral appliance alone that comprise the above-described mouthpieces. FIG. 13 is a perspective view of a presently preferred alternative embodiment of one such mouthpiece 100 and FIG. 14 is a perspective view of that mouthpiece 100 coupled to a treatment device 1042 that can comprise a ventilator, an inhaler, a pressurized air source, an anesthetic system, a therapeutic or corrective treatment system, and/or any medical or emergency treatment system/device. This presently preferred mouthpiece 100 comprises a continuous peripheral flexible wall 102 having an anterior section 104 and a plurality of posterior sections 106. Preferably, the inner and outer surfaces of the anterior and posterior sections 104 and 106 are adapted to the anatomy of a portion of a user's upper and/or lower dental arches. Preferably, the anterior section 104 encloses an orifice 108 that passes through the anterior section 104 and the retaining wings 110. While the orifice 108 is not limited to any dimensions, in some embodiments the orifice 108 allows for the passage of liquids without the removal of the mouthpiece 100 when it is placed in a user's mouth. Preferably, the orifice 108 is partially enclosed by a neck 112 that projects from an outer surface of the anterior section 104. Like the embodiments described above, the retaining wings 110 can comprise a unitary or a multi-part structure.

Figure 17:
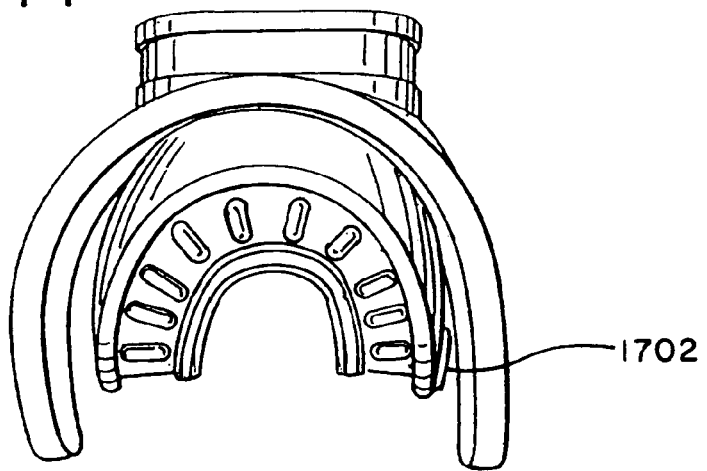
FIG. 17 is a side perspective view of a presently preferred alternative embodiment.

Preferably, the inner surfaces of the anterior and posterior sections 104 and 106 have a U-shape. A curved channel 114 extends along the inner surfaces from the orifice 108 to the ends 118 of the posterior sections 106. Preferably, the curved channel 114 aligns with a user's dental curve. Some presently preferred mouthpieces include one or multiple trays that fit substantially over the user's teeth covering the occlusal and portions of labial and lingual surfaces as shown in FIG. 17, and in some other embodiments, over most of the user's teeth surfaces to the gum lines. Other presently preferred mouthpieces include a plurality of bitewings 120 that divide a portion of the curved channel 114 into upper and lower channels as shown in FIG. 13. Preferably, each bitewing 120 or tray(s) includes a pair of upper and lower surfaces 122 and 124 that extend inward to an adjoining wall 126. While the upper and lower surfaces are shown as a unitary structure, alternative preferred embodiments include separate structure or trays adapted to the upper and the lower jaws. Preferably, the structures or trays couple the neck 112 and allow for lateral or vertical jaw adjustments. Preferably, these presently preferred embodiments allow the jaw(s) to be adjusted in predetermined increments.

In some presently preferred embodiments, adjustment hardware 1702 couples the upper and lower surfaces 122 and 124. The adjustment hardware 1702 allows a user or treatment provider to make lateral and/or vertical adjustments to the upper and/or lower jaws. The adjustment hardware 1702 can be coupled to any portion of the mouthpiece 100 including the bitewings 120 and/or one or both of the trays that couple a user's teeth. The adjustment hardware 1702 can be positioned near a cheek side molar as shown in FIG. 17, near an anterior section 104, or anywhere within or outside of the oral cavity. In one preferred embodiment, an adjustment knob coupled to the adjustment hardware projects from the anterior section 104 through the retaining wings 110 and the user's mouth to provide a mouthpiece that can be adjusted by a hand pressure.

As shown in FIG. 13, the upper and lower surfaces 122 and 124 of the bitewings 120 are substantially flat, although they also can comprise contoured upper and/or lower surfaces 122 and 124. Preferably, the contour comprises a sloping surface that substantially aligns with the chewing or biting surfaces of a user's teeth.

Referring to FIG. 13, preferably the upper and lower surfaces 122 and 124 of the bitewings 120 include a curved transition to a portion of the inner surfaces of the posterior sections 106 and the adjoining wall 126. Preferably, the adjoining wall 126 is spaced apart from the inner surface of the posterior section 106 and can be aligned with the inner dental curve or inner dental arch of the user. In one presently preferred embodiment, preferably the adjoining wall 126 can be positioned adjacent to or in contact with the inner surfaces of the user's teeth.

Figure 15:
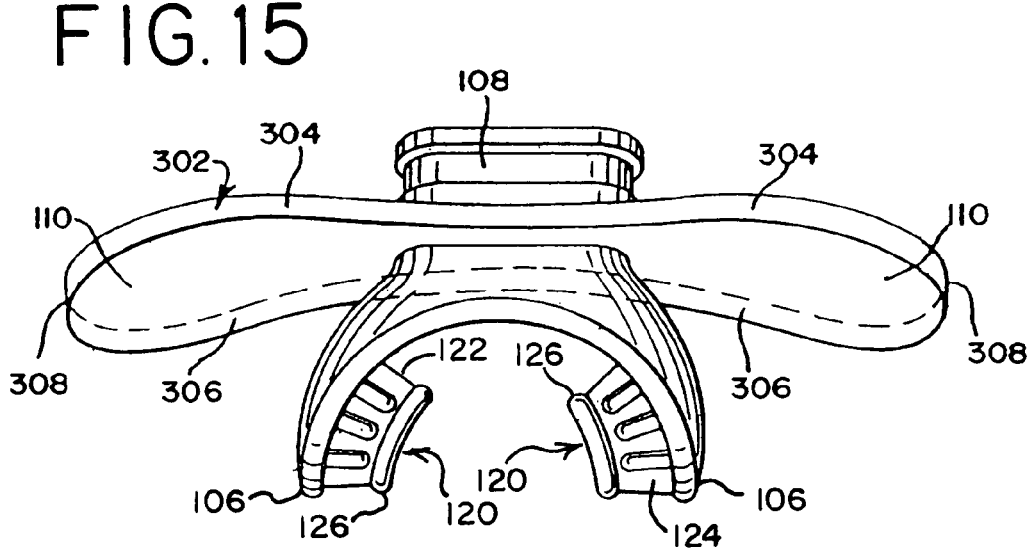
FIG. 15 is a side perspective view of a presently preferred alternative embodiment.

Preferably, the retaining wings 110 have a shape framed by a continuous surface 128 that can be positioned within a labial and/or buccal vestibule of the user. The labial and buccal vestibule is bounded in front and laterally by the user's lips and the continuous mucous membrane that lines the interior of the user's cheeks and behind and internally by the gums and teeth of the user's upper and lower jaws. As shown in FIGS. 15, preferably the upper rim 304 and the lower rim 306 of the retaining wings 110 each include double curve surfaces. The double curve surfaces comprise a concave surface joined to a pair of convex surfaces. In cross-section, the double curve surfaces are formed by the unison of a pair of convex lines to a concave line. As shown, preferably the upper, lower, and side rims 304, 306, and 308 that comprise a circular rim 302 allow the retaining wings 110 to substantially conform to the user's transition between the mucous membrane and the gums.

Referring to FIGS. 13 and 15, the retaining wings 110 are coupled to the neck 112 at a position intermediate of the anterior section 104 and a proximal rim 130. Alternatively, the retaining wings 110 can be a unitary part of or coupled to the anterior section 104 or neck 112. The retaining wings 110 comprise a pair of substantially flat surfaces 132 that are interconnected at the circular rim 302. Preferably, the retaining wings 110 are comprised of a flexible material. In the presently preferred embodiments, the retaining wings 110 are in contact with the user's lips and the continuous mucous membrane that lines the inner surfaces of the user's cheeks. Preferably, the bias of the retaining wings 110 increases when a continuous flow of fluids, such as compressed air passes through the orifice 108 into the user's mouth. In this presently preferred embodiment, the retaining wings 110 functions like a valve that facilitates the flow of fluids through the orifice 108. When in communication with a positive airway pressure, preferably the user's labial and buccal vestibule is pressurized. In one presently preferred embodiment, a gas such as an air pressure delivered through the orifice 108 into a user's mouth bias the retaining wings 110 that spread out the cheeks of the user and facilitates the user's orapharynx to relax and open, which facilitates unrestricted fluid flow.

Preferably, the presently preferred mouthpiece 100 can be altered without remaking the appliance. In one presently preferred embodiment, the retaining wings 110 can be adjusted by grasping the mouthpiece 110 and cutting the retaining wings 110 using a cutting device such as a scissors. Some presently preferred mouthpieces include weakened areas, such as perforations 1806 (shown in FIG. 18), that allow a user or treatment provider to customize the upper, lower, and side rims 304, 306, and 308 of the mouthpiece by hand. A tearing of the retaining wings 110 along these weakened areas can customize the retaining wings 110 to a user's mouth. Some presently preferred mouthpieces 100 can also be adjusted by placing the mouthpiece 100 in hot water making the mouthpiece 100 and trays moldable to a user's mouth. Preferably, as the mouthpiece 100 cools within a user's mouth, the mouthpiece stretches or shrinks to provide the user with an exact or almost exact fit. In alternative embodiments, only portions of the mouthpiece 100 are moldable.

Preferably, the outer periphery of the neck 108 is surrounded by a plurality of rings. Preferably, one of the rings extends around the orifice to form the proximal rim 130. Preferably, the rings allow the presently preferred embodiments to couple other devices. These devices can include one or more fluid lines such as a compressed gas line and also can include a humidifier, such as a heated humidifier to maintain oral hydration and/or a dispenser that delivers drugs or other treatments.

The presently preferred embodiments can be modified into many other alternative embodiments. For instance, multiple flow paths can also be partially enclosed within the orifice 108 or pass outside of the orifice 108 through the retaining wings 110. One such flow path is shown as a cylindrical shaped valve 1602 that is seated on the retaining wings 110. The valve 1602, which can also be formed within the retaining wings 110 and can have other shapes, provides access to the oral cavity and/or alimentary canal. Preferably, access to the alimentary canal can also be facilitated by a second orifice 1604 that passes through the flexible wall 102. While such access has many uses, in some preferred embodiments the valve 1602 provides access for suction or intubations. When used for intubations or receiving suction, an intubating device or suction device 1606 can pass through the valve 1602 and in some applications through the second orifice 1604.

Figure 16:
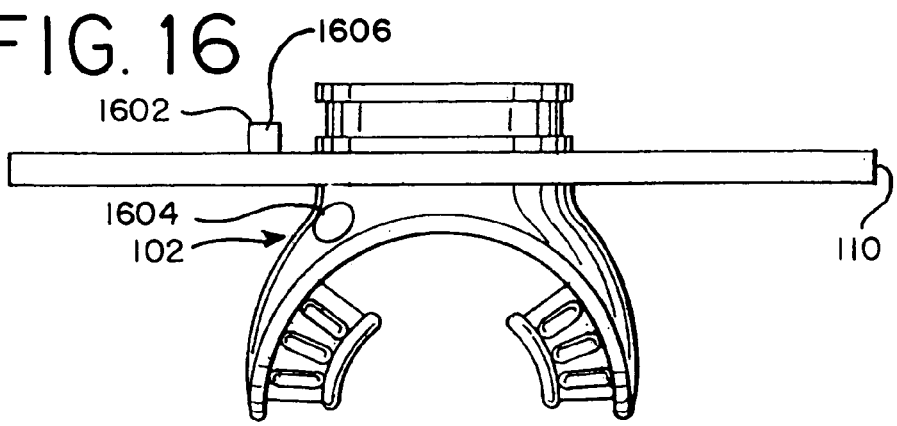
FIG. 16 is a side perspective view of a presently preferred alternative embodiment.

Preferably, the valve 1602 shown in FIG. 16 comprises a hollow flexible member or tube that is flush with or projects from the retaining wings 110. The flexible member or tube can have a uniform or varying inner circumference or diameter. A limiting device can be coupled to the flexible member or tube to control or regulates flow. Preferably, the limiting device controls a single or bidirectional flow. Effective limiting devices can include a flap or ball valve, for example.

In other alternative embodiments, an intubation tube 2002, such as an endotracheal intubation tube can be introduced into the mouth through the orifice 108 as shown in FIG. 20. A light source 2004, such as a fibreoptic light source, can be coupled to a power source 2006. The intubation tube 2002, which can comprise a single, double, and/or other multiple lumen tubes and can include a nasogastric tube for feeding. Preferably, this embodiment can be used in medical treatments that include, but are not limited to, thoracic anesthesia, ENT and dental surgery, nasal intubations in faciomaxillary surgery, etc. In some alternative embodiments, a holding device 1902, such as a clamp shown in FIG. 19, braces the neck 112 holding an intubation tube or any other device to the mouthpiece 100. Preferably, one or more openings 1802 passing through the retaining wings 110 can provide access to the oral cavity as shown in FIG. 18. In some embodiments the access may be used to suction out the mouth or to collect specimens.

The above-described presently preferred embodiments can be used with an open or closed breathing system and can be retained in a passive manner that does not require a biting force for mouthpiece 100 retention. Preferably, the presently preferred embodiments are retained in a user's mouth even when a user's jaw muscles are relaxed. Thus, the presently preferred embodiments facilitate a continuous fluid flow even when not retained by a biting pressure. When receiving a pressurized fluid flow through the orifice 108, the presently preferred embodiments maintain a positive pressure seal between the user's lips and the continuous mucous membrane that lines the interior of the user's cheeks and the retaining wings 110. Preferably, the presently preferred embodiments provide a watertight seal between the user's labial and buccal vestibule and the user's oral cavity when the preferred mouthpiece 100 is used underwater and a variable or airtight seal when the preferred mouthpiece 100 is used in firefighting, emergency, treatment, and/or medical applications.

While various embodiments of the invention have been described, it will be apparent to those of ordinary skill in the art that many more embodiments and implementations are possible that are within the scope of this invention. Accordingly, the invention is not to be restricted except in light of the attached claims and their equivalents.

I claim:

1. A mouthpiece comprising:
   a wall having an anterior and a plurality of posterior sections, the anterior and posterior sections having a portion adapted to be positioned adjacent to a dental arch;
   retaining wings coupled to the anterior section, a first portion of the retaining wings enclosing a portion of an orifice, and a second portion of the retaining wings adapted to an anatomy of a user's buccal vestibule; and
   a valve seated within the retaining wings.

2. The mouthpiece of claim 1 wherein the valve provides access to an alimentary canal.

3. The mouthpiece of claim 1 wherein the valve is in communication with an intubating device.

4. The mouthpiece of claim 1 wherein the valve is in communication with a medical device.

5. A breathing aide comprising:
   a wall having an anterior and a posterior section, the anterior and posterior sections having a portion adapted to positioned adjacent to a dental arch;
   retaining wings coupled to the anterior section, a first portion of the retaining wings enclosing a portion of an orifice, and a second portion of the retaining wings adapted to the anatomy of the user's buccal vestibule; and
   an adjustment member coupled to the wall that allows for the adjustment of one of an upper and a lower jaw.

6. The breathing aide of claim 5 further comprising a tray coupled to the adjustment member, wherein the tray is adapted to be positioned adjacent to a user's occlusal surfaces.

7. The breathing aide of claim 5 wherein the adjustment member is adapted to treat sleeping disorders.

8. The breathing aide of claim 5 wherein the adjustment member is adapted to treat medical disorders.

9. A breathing aide comprising:
   a wall having an anterior and a posterior section, the anterior and posterior sections having a portion adapted to positioned adjacent to a dental arch;
   retaining wings coupled to the anterior section, a first portion of the retaining wings enclosing a portion of an orifice, and a second portion of the retaining wings adapted to the anatomy of the user's buccal vestibule; and
   a tray coupled to the retaining wings;
   wherein the tray is adapted to facilitate a lateral adjustment of a user's jaw.

10. A breathing aide comprising:
    a wall having an anterior and a posterior section, the anterior and posterior sections having a portion adapted to positioned adjacent to a dental arch;
    retaining wings coupled to the anterior section, a first portion of the retaining wings enclosing a portion of an orifice, and a second portion of the retaining wings adapted to the anatomy of the user's buccal vestibule; and
    a tray coupled to the retaining wings;
    wherein the tray is adapted to facilitate a vertical adjustment of a user's jaw.

11. A breathing aide comprising:
    a wall having an anterior and a posterior section, the anterior and posterior sections having a portion adapted to positioned adjacent to a dental arch;
    retaining wings coupled to the anterior section, a first portion of the retaining wings enclosing a portion of an orifice, and a second portion of the retaining wings adapted to the anatomy of the user's buccal vestibule; and
    a tray coupled to an adjustment member and the retaining wings;
    wherein the adjustment member is configured to allow for the adjustment of the lower and the upper jaw.

* * * * *